United States Patent

Lhenry et al.

[11] Patent Number: 5,948,356
[45] Date of Patent: Sep. 7, 1999

[54] PROCESS FOR HIGH-PRESSURE STERILIZATION OF PRODUCTS

[75] Inventors: Bernard Lhenry, Le Creusot; Plantadis Rémy, Epinac, both of France

[73] Assignee: Framatome, Courbevoie, France

[21] Appl. No.: 08/994,320

[22] Filed: Dec. 19, 1997

Related U.S. Application Data

[62] Division of application No. 08/600,210, Feb. 12, 1996, Pat. No. 5,788,934.

[30] Foreign Application Priority Data

Feb. 15, 1995 [FR] France .................................... 95-01730

[51] Int. Cl.$^6$ ...................................................... A61L 2/00
[52] U.S. Cl. .............................. 422/39; 422/1; 422/295; 422/297; 422/300; 99/452; 99/461
[58] Field of Search ................................... 422/1, 39, 292, 422/295, 296, 297, 300; 99/452, 461

[56] References Cited

U.S. PATENT DOCUMENTS

| | | | |
|---|---|---|---|
| 2,069,820 | 2/1937 | Dodge | 422/39 |
| 5,165,325 | 11/1992 | Akatsu | 422/39 |
| 5,288,462 | 2/1994 | Carter et al. | 422/39 |
| 5,316,745 | 5/1994 | Ting et al. | 422/39 |
| 5,470,547 | 11/1995 | Lhenry | 422/295 |

FOREIGN PATENT DOCUMENTS

| | | |
|---|---|---|
| 0623353 A1 | 11/1994 | European Pat. Off. . |
| 26980854 | 11/1993 | France . |
| 9428745 | 12/1994 | WIPO . |

Primary Examiner—Elizabeth McKane
Assistant Examiner—Fariborz Moazzam
Attorney, Agent, or Firm—Pollock, Vande Sande & Priddy

[57] ABSTRACT

A semi-continuous process for high-pressure sterilization of a liquid or solid product, in which the sterilization of successive volumes of the product is performed by compressing the product at high pressure in a variable treatment chamber of generally tubular shape and of circular cross-section.

2 Claims, 8 Drawing Sheets

FIG. 7H

PROCESS FOR HIGH-PRESSURE STERILIZATION OF PRODUCTS

CROSS-REFERENCE TO RELATED APPLICATIONS

This is a divisional of U.S. Ser. No. 08/600,210, filed Feb. 12, 1996 (now U.S. Pat. No. 5,788,934).

FIELD OF THE INVENTION

The subject of the present invention is a semi-continuous process for high-pressure sterilization of a liquid or solid product.

In order to sterilize products, it is known to subject them to a pressure which may reach a value of the order of 8000 bar.

For this purpose, a sealed container of small volume is used in which the products to be sterilized, which are subjected to a high pressure, are placed. This sealed container is connected to a pump intended to inflate the interior of the container for the purpose of increasing the internal pressure.

In the case of a fluid to be sterilized, this fluid is contained in a sealed container and subjected directly to the desired pressure obtained by the use of the pump.

In the case of a packaged element to be sterilized, this element is placed in the sealed container and is subjected to the required pressure by means of the pump.

However, the processes employed to date do not enable large quantities of products to be sterilized.

The invention provide a semi-continuous process for high-pressure sterilization of a liquid or solid product enabling large quantities of products to be sterilized and having all the necessary safety guarantees, while at the same time ensuring that the sterilized product maintains its original qualities, such as its taste and its appearance.

The subject of the invention is a semi-continuous process for the high-pressure sterilization of a liquid or solid product, in which the sterilization of successive volumes of a product is performed in a variable treatment chamber of generally tubular shape and of circular cross-section, having two open ends opposite each other, by carrying out the following steps:

a first separator of cross-section corresponding to the cross-section of the chamber is inserted at the first end of the chamber;

the second end of the chamber is closed off;

a first volume of the product to be sterilized is injected into the chamber, at the first end, so as to fill the said chamber and to move the first separator to the second end;

a second separator of cross-section corresponding to the cross-section of the chamber is inserted into the chamber at the first end;

the first volume of the product is compressed to the desired pressure in order to sterilize this first volume of the product;

the second end of the chamber is opened;

the first separator and the first volume of the sterilized product are discharged from the chamber by injecting, at the first end of the chamber, a second volume of the product to be sterilized;

the first separator and the first volume of the sterilized product are recovered;

the first end of the chamber is sterilized after each volume of the product has been injected;

an airlock for recovering the separators is sterilized after each volume of the sterilized product has been recovered;

the first separator is cleaned; and after the second end of the chamber has been closed and the second volume of the product to be sterilized has been injected into the said chamber, the first separator is inserted into the chamber at the first end and the cycle is repeated for the entire product to be sterilized.

The characteristics and advantages of the invention will appear in the course of the following description, which is given solely by way of example, in conjunction with the appended drawings, in which.

DETAILED DESCRIPTION

The figures show a semi-continuous machine for high-pressure sterilization of a liquid or solid product, such as fluids or foods.

Figure 1:
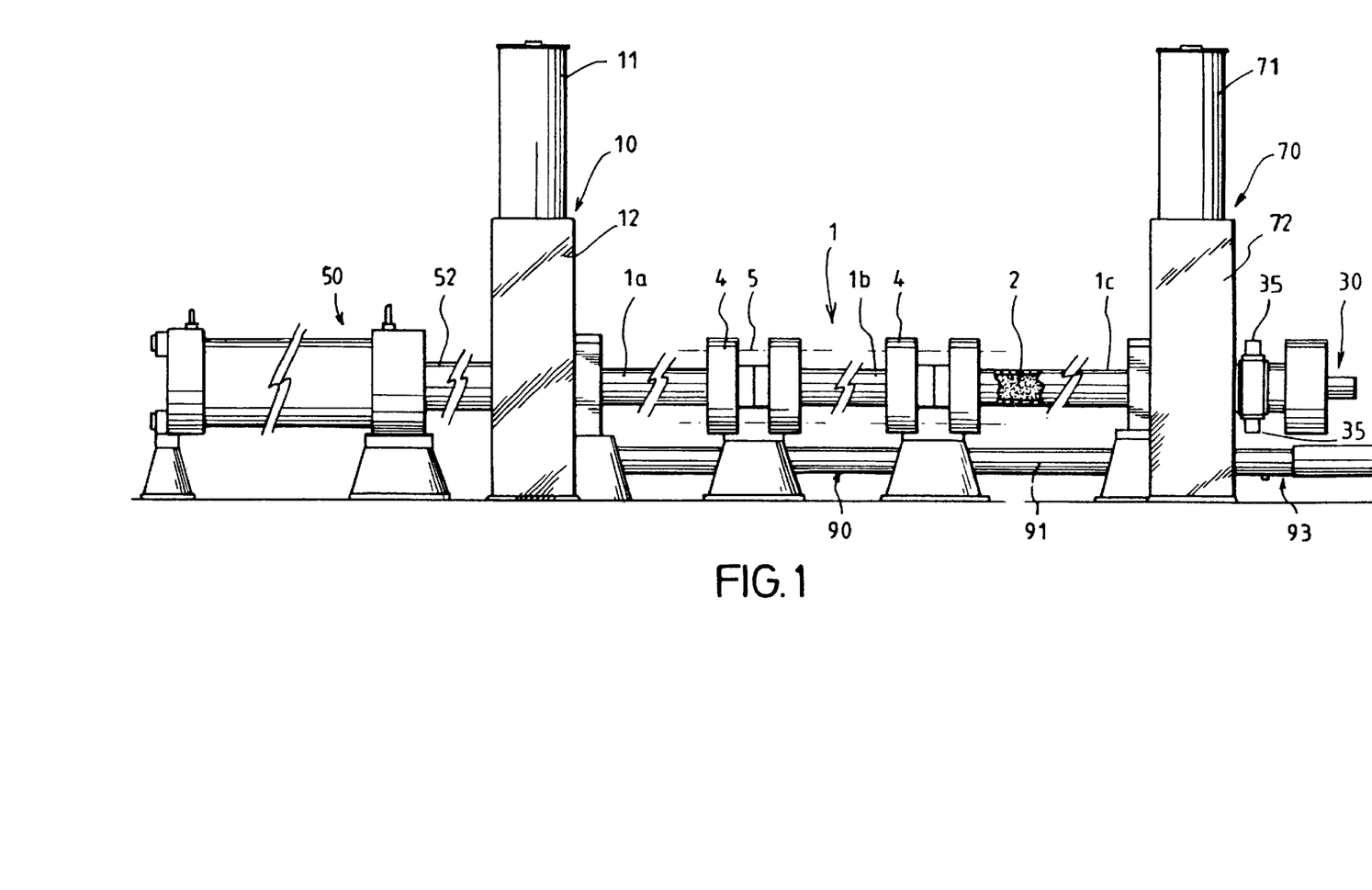
FIG. 1 is a schematic view of a machine for high-pressure sterilization of a product.

The sterilization machine shown in FIG. 1 comprises:

a tube 1 of variable length forming an internal treatment chamber 2, of circular cross-section and having two open ends 2a and 2b opposite each other;

means 10 for injecting successive volumes of the product to be sterilized into the chamber, these means being arranged at the first end 2a of the chamber 2;

means 30 for closing off the second end 2b of the chamber 2;

means 50 for compressing the successive volumes of the product in order to sterilize the said product;

means 3 for separating the volume of the sterilized product from the volume of the product to be sterilized;

means 25 and 26 for sterilizing the first end 2a of the chamber 2;

means 70 for recovering the successive volumes of the sterilized product, these means being arranged at the second end 2b of the chamber 2;

airlocks 92 and 110 for recovering the separating means 3;

means 85 for sterilizing the recovery airlock 92;

and means 90 for transferring the separating means 3 from one end of the chamber 2 to the other.

As shown in FIG. 1, the tube 1 of variable length is formed by several independent tubular elements 1a, 1b, 1c, etc. fixed end to end by means of connecting flanges 4 which are fixed together, for example, by bolts 5.

A seal (not shown) is arranged at the interface of the associated tubular elements 1a, 1b, 1c, etc.

Figure 2:
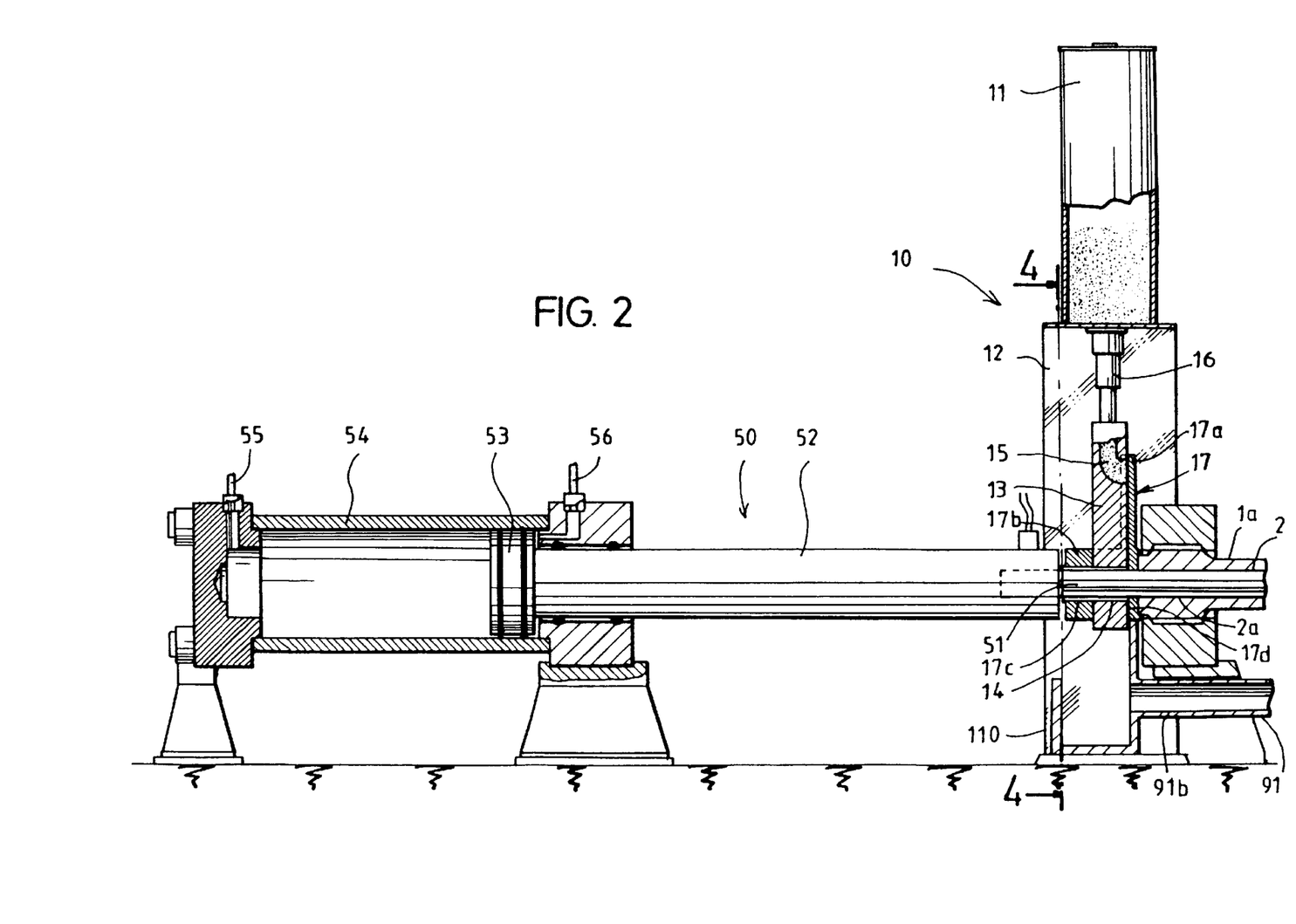
FIG. 2 is a schematic sectional view of the means for injecting the product into the treatment chamber of a sterilization machine and for compressing this product.
Figure 3:
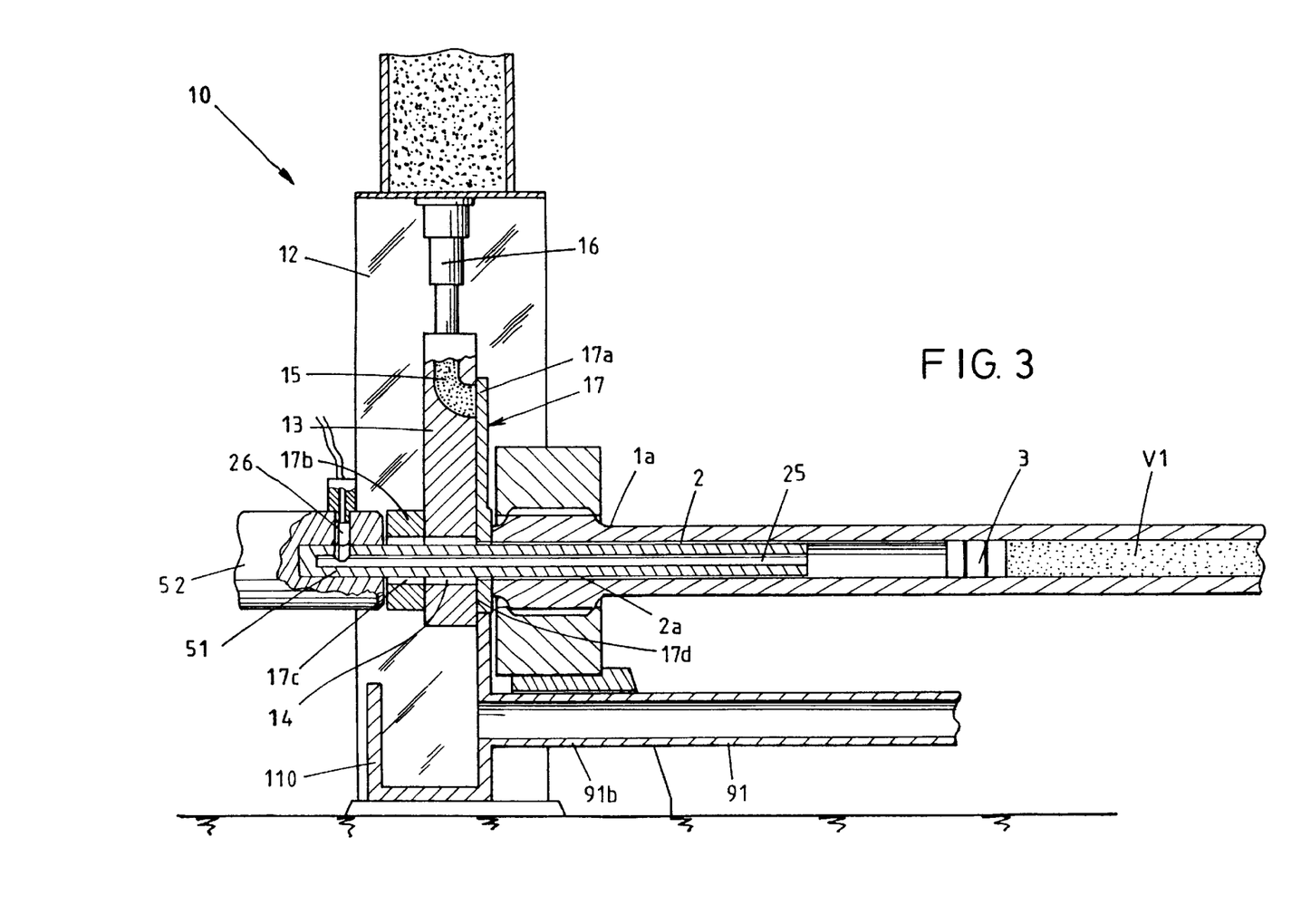
FIG. 3 is a sectional view, on a larger scale, of the means for injecting the product and for compressing this product.
Figure 4:
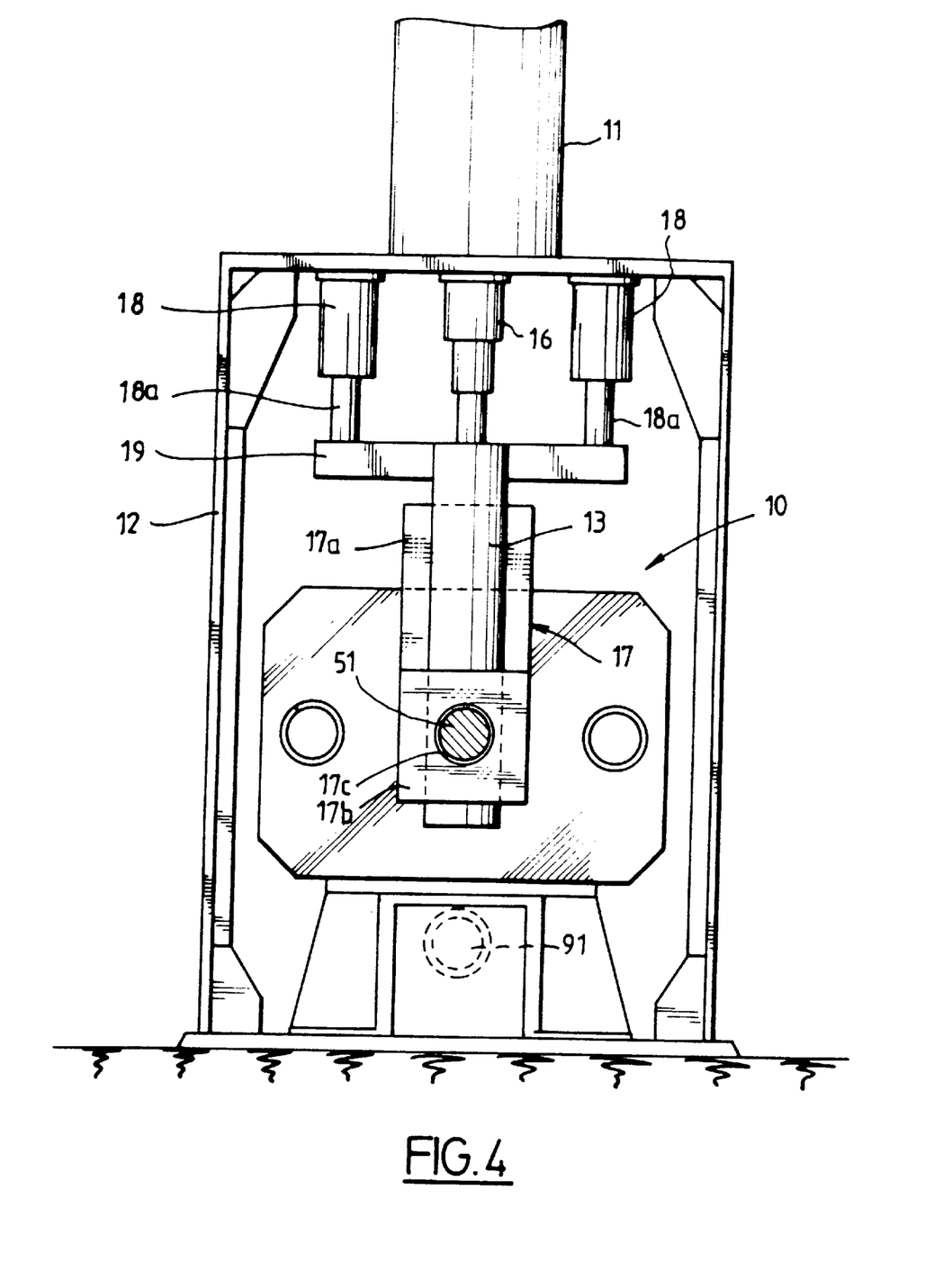
FIG. 4 is a sectional view along line 4—4 in FIG. 2.

Referring to FIGS. 2 to 4, the means 10 for injecting the product to be sterilized into the treatment chamber 2 will now be described.

These injection means 10 consist of a pressurized feed reservoir 11 containing the product to be sterilized and fixed on a base 12.

The injection means 10 also comprise a filling slide valve 13 formed by a plate of rectangular cross-section having, at its lower part, a transverse hole 14 and, at its upper part, a channel 15 for flow of the product to be sterilized communicating with the pressurized feed reservoir 11 via a telescopic pipe 16.

The filling valve 13 can be moved vertically by a control member between a first position bringing the transverse hole 14 into communication with the chamber 2 and a second position bringing the flow channel 15 into communication with the said chamber 2.

To this end, the slide valve 13, while it is moving vertically, is guided by a piece 17 fixed on the end 2a of the tube 1a.

The piece 17 is formed by a vertical plate 17a on which the slide valve 13 slides and by a bush 17b having a horizontal bore 17c arranged along the axis of the chamber 2 and a diameter corresponding to that of chamber 2, and a vertical passage 17d have a cross-section corresponding that of the slide valve 13 and intended for slide valve 13 to slide in.

The member for controlling the movement of the slide valve 13 consists of at least one cylinder actuator 18 and preferably two vertical cylinder actuators 18 parallel to each other and supported by the base 12. The rod 18a of each cylinder actuator 18 is fastened to a base/plate 19 fixed to the upper part of the slide valve 13.

The machine also includes means, shown in FIG. 3, for sterilizing the first end 2a of the treatment chamber 2.

These sterilizing means are formed by a channel 25 provided in the piston 51 and emerging at the free end of piston 51. The channel 25 is connected via a hole 26 to means (not shown) for injecting steam so as to sterilize the end 2a of the chamber 2, as will be explained hereinbelow.

Figure 5:
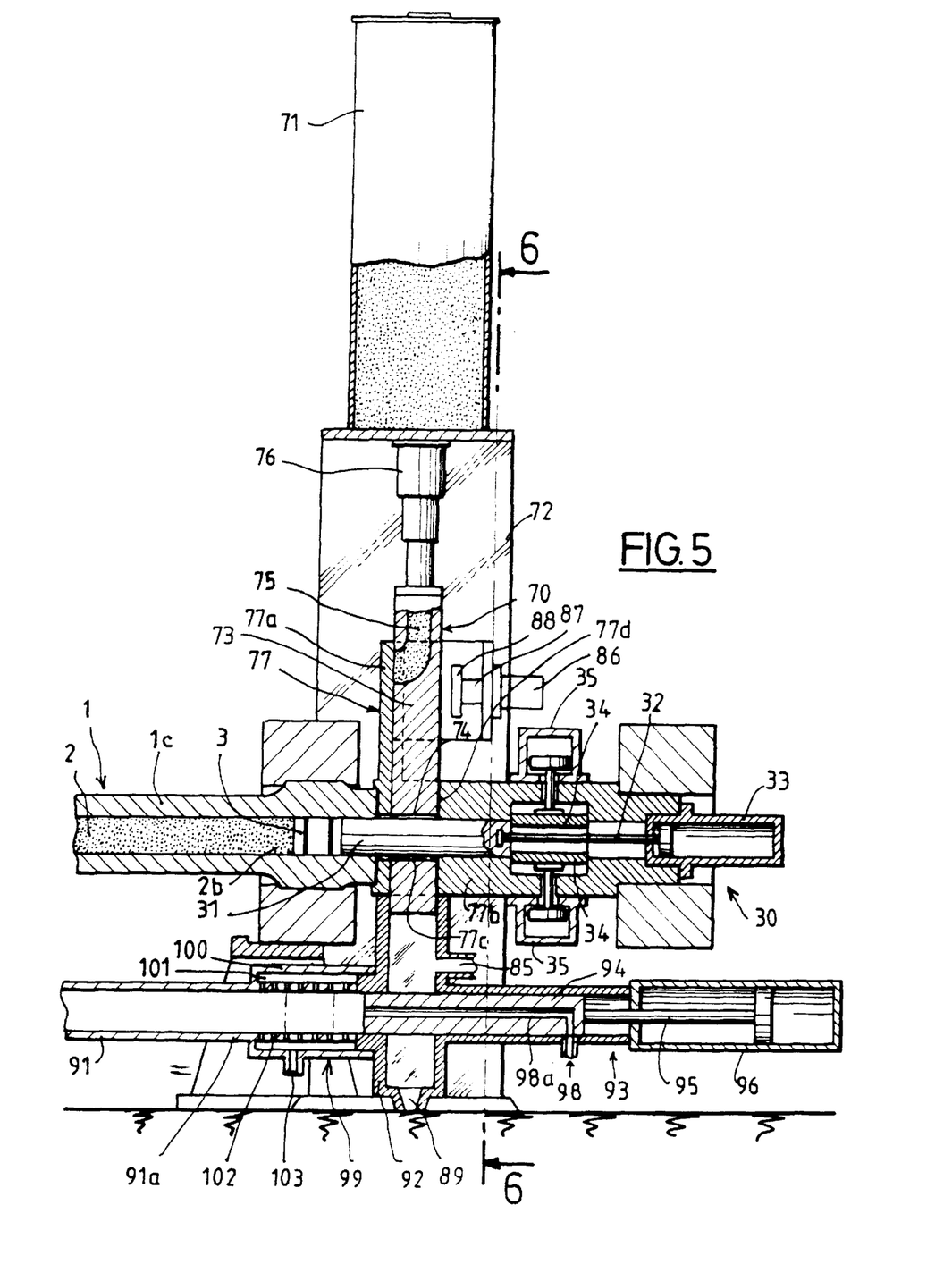
FIG. 5 is a schematic sectional view, on a larger scale, of the means for recovering the sterilized product and the means for transferring the separating cylindrical separators of the sterilization machine.

As shown in FIG. 5, the means 30 for closing off the second end 2b of the treatment chamber 2 comprise a piston 31 of circular cross-section which is mounted at the end of a rod 32 of a cylinder actuator 33.

The piston 31 can move horizontally between a first position in which the free end of the piston 31 is placed in the treatment chamber 2 and a second position in which the free end of the piston 31 is located outside chamber 2.

The piston 31 is associated with means for locking the piston 31 in the position in which the chamber 2 is closed off, which means consist of two jaws 34 opposite each other and each controlled by a cylinder actuator 35.

The jaws 34 can move vertically between a position in which the piston 31 is blocked, as shown in FIG. 5, and an unlocked position in which the piston 31 is released.

As shown in FIGS. 2 and 3, the means 50 for compressing the product in the treatment chamber 2 consist of a piston 51 of circular cross-section and of diameter corresponding to the diameter of the treatment chamber 2.

The piston 51 is fixed to the free end of a rod 52 having, at its end on the side opposite to that on which the piston 51 is fixed, a control piston 53 of a cylinder actuator 54.

Conventionally, the cylinder actuator 54 includes conduits 55 and 56 for supplying pressurized fluid.

The piston 51 can move horizontally along the axis of the treatment chamber 2 between a first position in which the free end of this piston 51 is inserted into the treatment chamber 2 passing through the transverse hole 14 in the slide valve 13, as shown in FIG. 2, and a second position in which the free end of the piston 51 is retracted and positioned outside the chamber 2 and the horizontal bore 14 of the slide valve 13.

Figure 6:
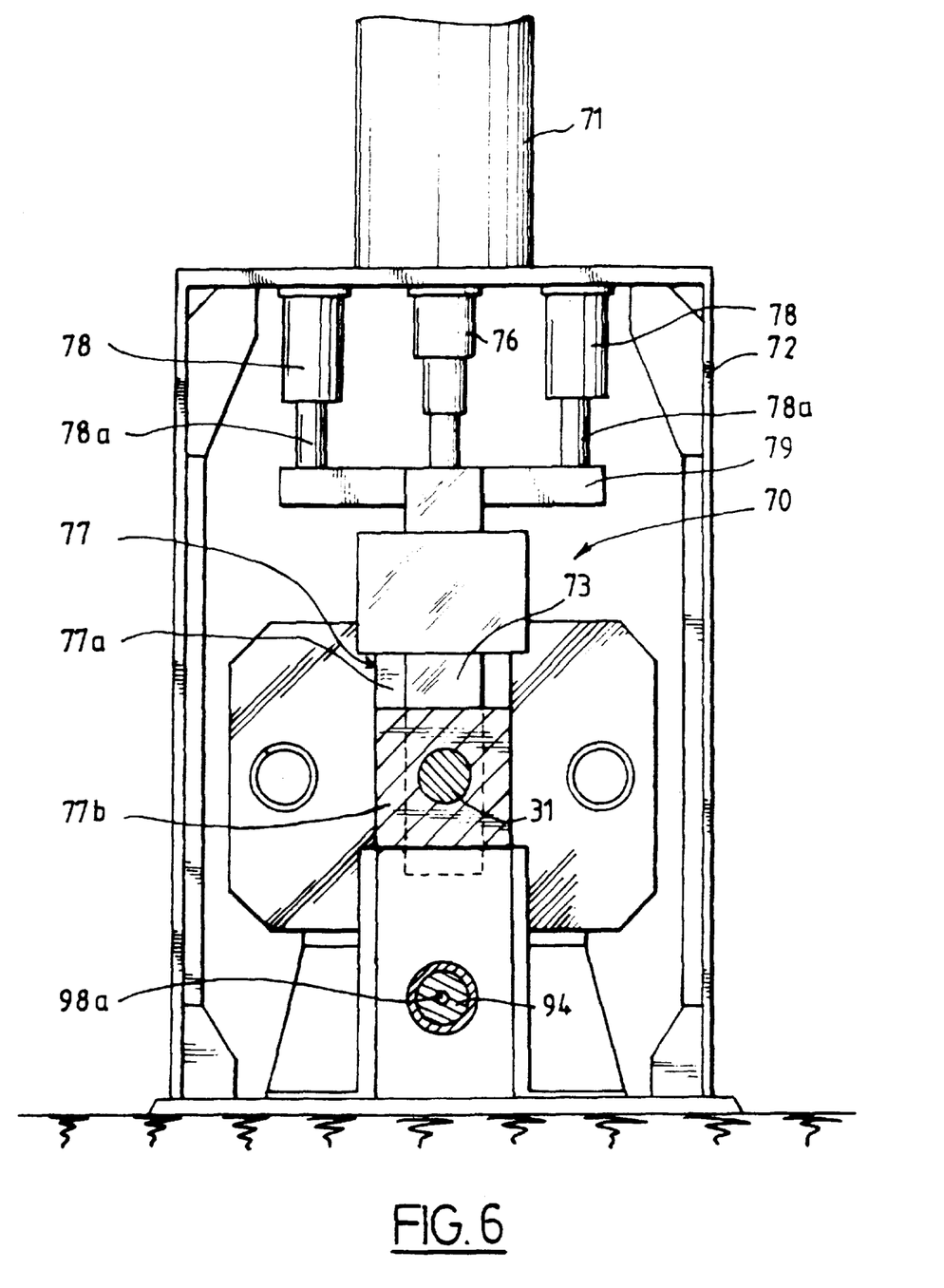
FIG. 6 is a sectional view along line 6—6 in FIG. 5.

As is apparent in FIGS. 5 and 6, the means 70 for recovering the sterilized product are formed by a sterile recovery reservoir 71 supported by a base 72.

The recovery means 70 also comprise an emptying slide valve 73 formed by a plate of rectangular cross-section having, at its lower part, a transverse hole 74 through which the closing-off piston 31 passes and, at its upper part, a flow channel 75 communicating with the recovery reservoir 71 via a telescopic pipe 76.

The recovery slide valve 73 can move vertically by means of a control member between a first position bringing the transverse hole 74 into communication with the chamber 2 and a second position bringing the flow channel 75 into communication with the said chamber 2.

To this end, the slide valve 73, while it is moving vertically, is guided by a piece 77 fixed on the end 2b of the tube 1c.

The piece 77 is formed by a vertical plate 77a on which the slide valve 73 slides and by a bush 77b having a horizontal bore 77c arranged along the axis of the treatment chamber 2 and a vertical passage 77d having a cross-section corresponding to that of the slide valve 73 and intended to enable the slide valve 73 to slide vertically between the two positions.

As shown in FIG. 6, the member for controlling the movement of the slide valve 73 consists of at least one cylinder actuator 78 and preferably of two vertical cylinder actuators 78 supported by the base 72.

The rod 78a of each cylinder actuator 78 is fastened to a base/plate 79 fixed to the upper part of the said slide valve 73.

The bush 77b of the piece 77 serves as a member for guiding the piston 31 and as a member for supporting the cylinder actuator 33 and the two cylinder actuators 35 for controlling the jaws 34.

The sterilization machine as described above enables successive volumes of product to be sterilized and includes, for this purpose, means 3 for separating the volume of the sterilized product from the volume of the product to be sterilized.

These separating means are formed by several independent cylindrical separators of diameter corresponding to the diameter of the chamber 2 and including members for sealing to the wall of the said chamber 2.

These cylindrical separators 3 are intended to be moved from the end 2a to the end 2b of the treatment chamber 2 between each volume of product and to be recycled from the second end 2b to the first end 2a of the treatment chamber 2.

To this end, the machine includes means 90 for transferring the cylindrical separators 3 from one end of the chamber 2 to the other.

Referring to FIGS. 1, 2 and 5, these means 90 for transferring the cylindrical separators 3 will now be described.

The means 90 for transferring the cylindrical separators are formed by a return pipe 91 arranged beneath the tube 1 and extending over the entire length of tube 1.

The return pipe 91 includes, at its end 91a located beneath the end 2b of the tube 2, an airlock 92 connected to end 2b of the tube 1 via the emptying slide valve 73.

The machine includes means for sterilizing the airlock 92 for recovering the separators 3. These means are formed by a hole 85 provided in one wall of the said airlock 92 and connected to means, not shown, for injecting steam.

While the airlock 92 is being sterilized by steam injected via the hole 85, the emptying slide valve 73 is pressed against the vertical plate 77*a* so as to seal off the flow channel 75.

In order to do this, the base 72 supports a cylinder actuator 86 which includes a rod 87 whose free end is provided with a plate 88 intended to bear on the slide valve 73 in order to apply slide valve 73 against the vertical plate 77*a* while the airlock 92 is being sterilized.

In addition, the bottom of the airlock 92 is equipped with a hole 89 for removing the soiled material during the sterilization of the airlock 92.

The pipe 91 also comprises, at its end 91*a*, a member 93 for inserting the cylindrical separators 3 into the return pipe 91, means 98 for propelling the cylindrical separators 3 in the return pipe 91, and means 99 for cleaning the cylindrical separators 3.

The member 93 for inserting the cylindrical separators 3 into the return pipe 91 is formed by a iston 94 fixed to the free end of a rod 95 of a cylinder actuator 96.

The piston 94 can move horizontally between a first position in which its free end enters the return pipe 91, passing through the airlock 92, and a second position in which the free end of the piston 94 is located outside the airlock 92.

The means 98 for propelling the cylindrical separators 3 in the return pipe 91 are formed by a channel 98*a* which passes over its entire length through the piston 94 and which emerges at the free end of piston 94.

This conduit 98*a* is connected to a supply (not shown) of a pressurized fluid.

The cleaning means 99 comprise a sleeve 100 which is arranged around the end 91*a* and determines a chamber 101 in which the return pipe 91 is pierced by a multiplicity of small holes 102.

The chamber 101 is connected via a conduit 103 to means (not shown) for supplying a fluid for cleaning and sterilizing the cylindrical separators 3.

The end 91*b* of the return pipe 91 located beneath the end 2*a* of the chamber 2 of the tube 1 includes an airlock 110 for recovering the cylindrical separators 3 and communicating with the end 2*a* of the chamber 2 via the slide valve 13 for transferring the cylindrical separators from the return pipe 91 into the treatment chamber 2.

The airlock 110 also serves as a chamber for recovering the water arising from the injecting of steam at the end 2*a* of the chamber 2.

Referring now to FIGS. 7A to 7H, the operation of the sterilization machine will now be described.

Figure 7A:
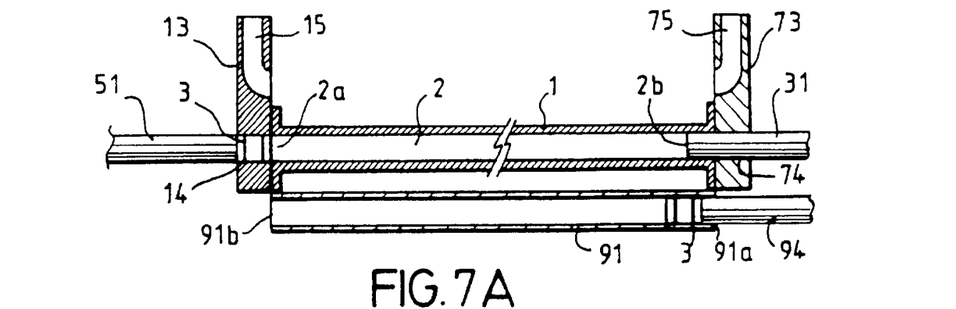
FIGS. 7A to 7H are diagrams showing the various steps in the operation of the sterilization machine according to the invention.

First, as shown in FIG. 7A, the feed slide valve 13 is in the up position so that the transverse hole 14, in which a cylindrical separator 3 has been placed, is in alignment with the chamber 2.

The recovery slide valve 73 is also in the up position and the end 2*b* of the chamber 2 is closed off by the piston 31 which passes through the transverse hole 74 in slide valve 73.

A second cylindrical separator 3 is held in readiness in the end 91*a* of the return pipe 91.

The piston 51 of the cylinder actuator 54 is moved in order to insert the first cylindrical separator 3 into the treatment chamber 2.

Figure 7B:
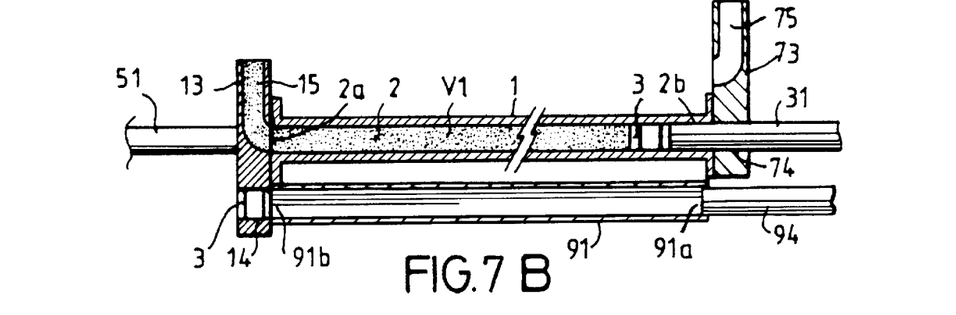
Figure 7C:
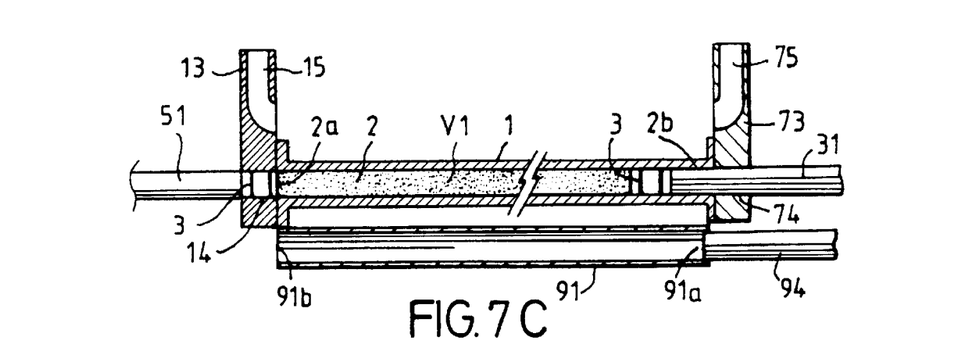

Next, the piston 51 is brought back into the initial position and the feed slide valve 13 is brought into the down position in order to bring the feed reservoir 11 into communication with the treatment chamber 2 via the telescopic pipe 16 and the flow channel 15, as shown in FIG. 7B.

A first volume V1 of product to be sterilized is injected into the chamber 2, moving the first cylindrical separator 3 as far as the piston 31.

Simultaneously, the pressurized fluid is injected into the return pipe 91 via the conduit 98*a* of the piston 94. This has the effect of moving the second cylindrical separator 3 in this return pipe 91 and of placing the said second cylindrical separator 3 in the transverse hole 14 in the slide valve 13.

Figure 7D:
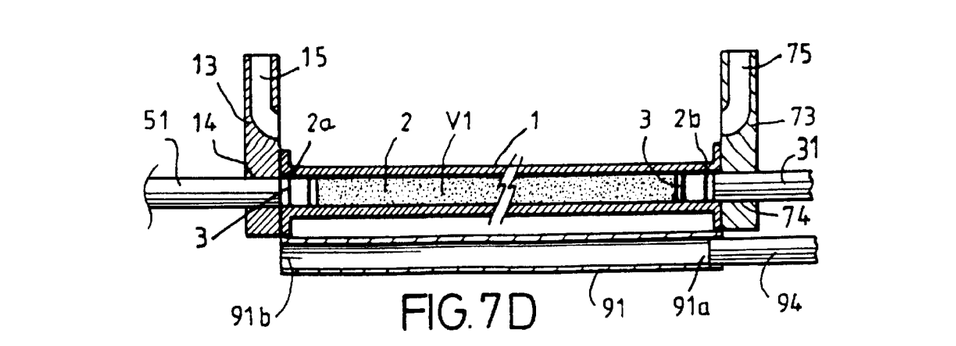
Figure 7E:
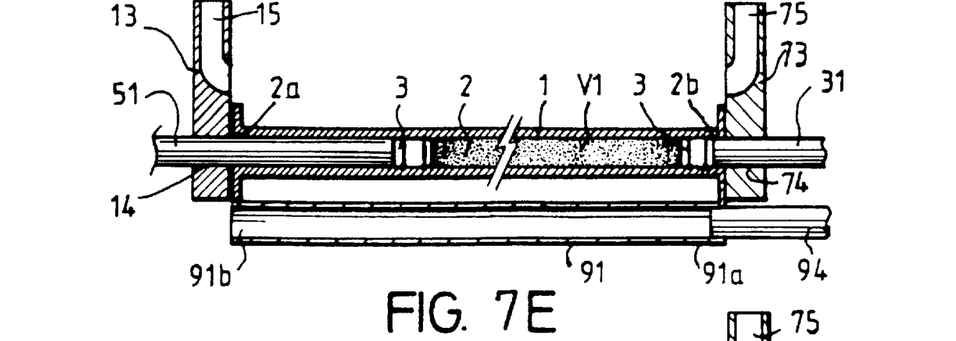

When the first volume V1 of the product to be sterilized has been injected into the treatment chamber 2, the feed slide valve 13 is placed in the up position and the piston 51 of the cylinder actuator 54 is moved horizontally towards the treatment chamber 2 so as to insert the second cylindrical separator 3 into this treatment chamber and to compress the first volume V1 of the product to a defined pressure (FIGS. 7D and 7E).

Figure 7F:
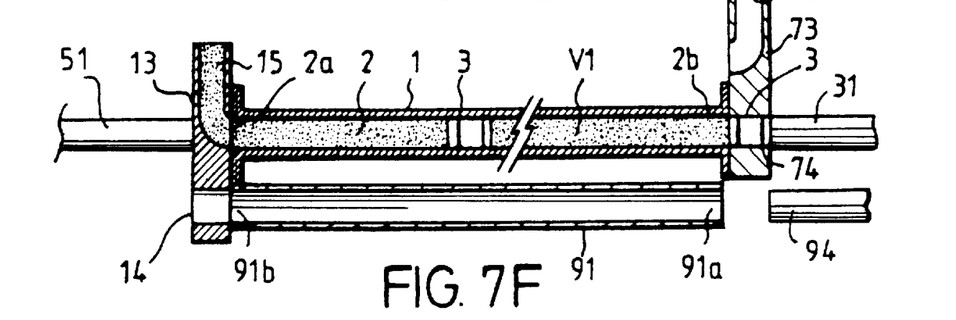

As soon as the first volume V1 of the product has been compressed, and therefore sterilized, the pressurizing piston 51 is brought back out of the treatment chamber 2, the filling slide valve 13 is placed in the down position so as to bring the reservoir 11 once again into communication with this treatment chamber via the telescopic pipe 16 and the feed channel 15, and then the closing-off piston 31 is brought back out of the treatment chamber 2, as shown in FIG. 7F.

While the piston 51 is returning to its initial position, steam is injected via the hole 26 and the channel 25, the volume V1 of the product and the second separator 3 forming a sealing plug.

The steam flows in the channel 25, then enters the end 2*a* of the chamber 2 and returns via the functional clearance existing between the piston 51 and the chamber 2, this having the effect of sterilizing the end 2*a* of chamber 2 before injecting a new volume of the product.

The water is recovered in the airlock 110.

This sterilization is performed between each injection of the product to be sterilized and steam continues to be injected during the time necessary to achieve adequate sterilization.

Figure 7G:
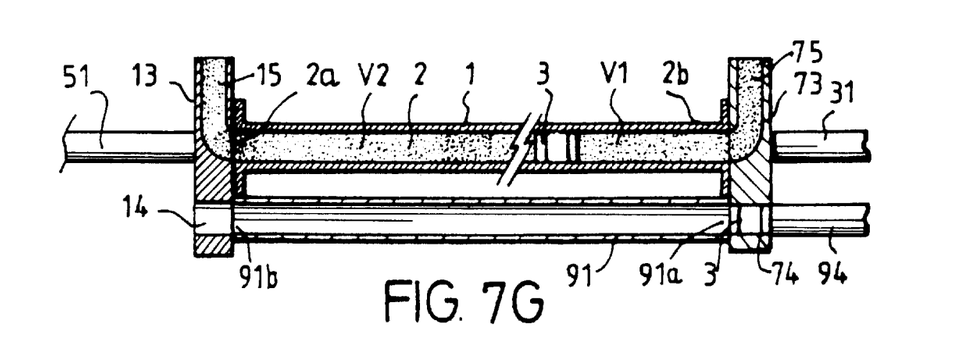
Figure 7H:
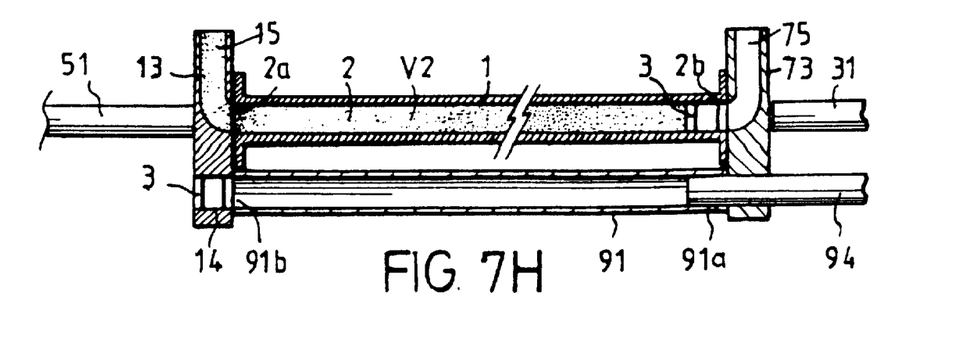

The recovery slide valve 73 is placed in the down position in order to bring the treatment chamber 2 into communication with the sterile recovery reservoir 71 and to position the first cylindrical separator 3 in the alignment of the return pipe 91, as may be seen in FIG. 7G.

Next, a second volume V2 of the product to be treated is injected into the treatment chamber 2 from the feed reservoir 11, thus transferring the first volume V1 of the sterilized product into the recovery reservoir 71 and moving the second cylindrical separator 3 to the end 2*b* of the treatment chamber 2.

In addition, between each recovery of the sterilized product, steam is injected via the hole 85 in order to sterilize the airlock 92 and recover the soiled material via the hole 89.

During this injection of steam, the cylinder actuator 86 is actuated so that, through the effect of the thrust exerted by the rod 87, the plate 88 comes to bear on the slide valve 73.

Thus, the slide valve 73 is pressed against the vertical plate 77*a* and the flow channel 75 is sealed off.

Simultaneously, the piston 94 is moved horizontally in order to transfer the second cylindrical separator 3 from the airlock 92 into the cleaning chamber 101 into which a cleaning and sterilizing fluid is injected.

Once the second cylindrical separator 3 has been cleaned and sterilized, the pressurized fluid is injected via the conduit 98*a* in the piston 94 in order to move this second cylindrical separator 3 in the return pipe 91 and place it in readiness in the transverse hole 14 in the slide valve 13.

When the second volume V2 of product is sterilized, the cycle starts again and is repeated until all of the product has been sterilized.

Each volume of the product is compressed to a pressure of between 5000 and 8000 bar.

By using a variable treatment chamber, the high-pressure sterilization machine according to the invention makes it possible to sterilize large volumes of product, such as liquid or solid products for example, while at the same time providing all the safety guarantees which are absolutely essential when using very high pressure.

In addition, the sterilization process and according to the invention enable the sterilized product to maintain its original qualities, such as its taste and its appearance.

We claim:

1. A semi-continuous process for the high-pressure sterilization of a liquid or solid product, wherein the sterilization of successive volumes of the product is performed in a generally tubular variable treatment chamber of circular cross-section and having opposite first and second open ends, said process comprising the steps of:

(a) inserting a first separator having a cross-section corresponding to a cross-section of the chamber at said first end of the chamber;
   (b) closing off said second end of said chamber;
   (c) injecting a first volume of the produce to be sterilized into the chamber at said first end, so as to fill said chamber and to move said first separator to said second end;
   (d) inserting a second separator having a cross-section corresponding to the cross-section of the chamber into the chamber at said first end;
   (e) compressing said first volume of the product to a desired pressure in order to sterilize said first volume of the product;
   (f) opening said second end of the chamber;
   (g) discharging said first separator and said first volume of the sterilized product from the chamber by injecting, at said first end of said chamber, a second volume of the product to be sterilized;
   (h) recovering said first separator and said first volume of the sterilized product;
   (i) sterilizing said first end of the chamber after each volume of the product has been injected;
   (j) sterilizing an airlock for recovering the separators after each volume of the sterilized product has been recovered;
   (k) cleaning said first separator; and
   (l) after said second end of the chamber has been closed and said second volume of the product to be sterilized has been injected into said chamber, inserting said first separator into the chamber at said first end and repeating the cycle for the entire product to be sterilized.

2. The process according to claim 1, wherein each volume of the product is compressed in succession to a pressure of between 5000 and 8000 bar.

* * * * *

UNITED STATES PATENT AND TRADEMARK OFFICE
CERTIFICATE OF CORRECTION

PATENT NO. : 5,948,356
DATED : September 7, 1999
INVENTOR(S): Bernard Lhenry and Rémy Plantadis It is certified that error appears in the above-identified patent and that said Letters Patent is hereby corrected as shown below: On the title page: Item

[75] The name of the second inventor has been reversed, please replace with --Rémy Plantadis--.

Signed and Sealed this

First Day of February, 2000

Attest:

Q. TODD DICKINSON

Attesting Officer

Acting Commissioner of Patents and Trademarks